United States Patent [19]

Rubin et al.

[11] 4,444,202

[45] Apr. 24, 1984

[54] BREATHING EXERCISER

[76] Inventors: Howard Rubin, 1937 Nester St., Philadelphia, Pa. 19115; Brent Weinerman, 897 Bridge St., Philadelphia, Pa. 19124

[21] Appl. No.: 369,174

[22] Filed: Apr. 16, 1982

Related U.S. Application Data

[63] Continuation-in-part of Ser. No. 363,793, Mar. 31, 1982.

[51] Int. Cl.³ ............................ A61B 5/08; A63B 23/00
[52] U.S. Cl. ........................................ 128/725; 272/99
[58] Field of Search ............................. 128/725–730, 128/205.16; 272/99

[56] References Cited

U.S. PATENT DOCUMENTS

| | | | |
|---|---|---|---|
| 3,695,608 | 10/1972 | Hanson | 272/99 |
| 4,025,070 | 5/1977 | McGill et al. | 128/727 |
| 4,037,836 | 7/1977 | Puderbaugh et al. | 272/97 |
| 4,114,608 | 9/1978 | Russo | 128/725 |
| 4,170,228 | 10/1979 | Elson et al. | 128/725 |
| 4,221,381 | 9/1980 | Ericson | 272/99 |
| 4,232,683 | 11/1980 | Bartholomew et al. | 128/725 |
| 4,284,083 | 8/1981 | Lester | 272/99 |

OTHER PUBLICATIONS

Advertisement Entitled "Tri Flo II Incentive Deep--Breathing Exerciser"-Chesebrough-Ponds, Inc., 2 pp., Undated.
Advertisement Entitled "New Voldyne, The First Volumetric Lung Exerciser Designed For Hand-Held Use"-Chesebrough-Ponds, Inc. 1 p., Undated.

*Primary Examiner*—Henry J. Recla
*Assistant Examiner*—Karin M. Reichle
*Attorney, Agent, or Firm*—Steele, Gould & Fried

[57] ABSTRACT

A breathing exerciser, comprising: first and second tubes; a lower cap member having bores for receiving one end of each of the tubes, the lower cap member having a passageway communicating between the first tube and a lower inlet/outlet opening; an upper cap member having bores for receiving the other ends of the tubes, and having a passageway communicating between both the tubes and an upper inlet/outlet opening; a floor member closing the lower end of the second tube; a floatable indicating member disposed in the second tube, the indicating member being upwardly movable during fluid flow into the upper inlet/outlet opening, through the first tube and out of the lower inlet/outlet opening, the amount of upward movement depending upon the rate of fluid flow; a valve assembly for adjusting the effective size of at least one of the inlet/outlet openings, for controlling the fluid flow rate required to move the indicating member over an effective range; and, openings in the second tube for calibrating the effective range, whereby the volume of air inhaled through the exerciser can be monitored and controlled.

7 Claims, 12 Drawing Figures

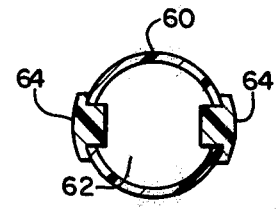
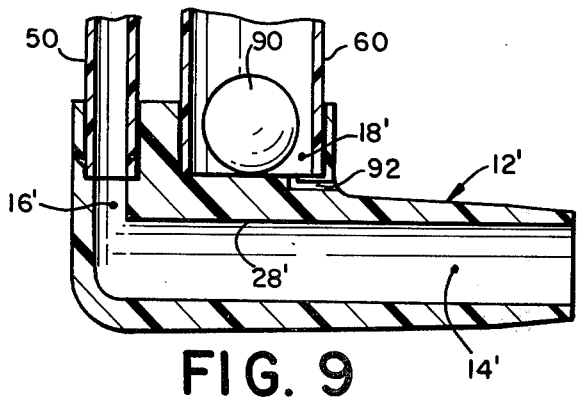
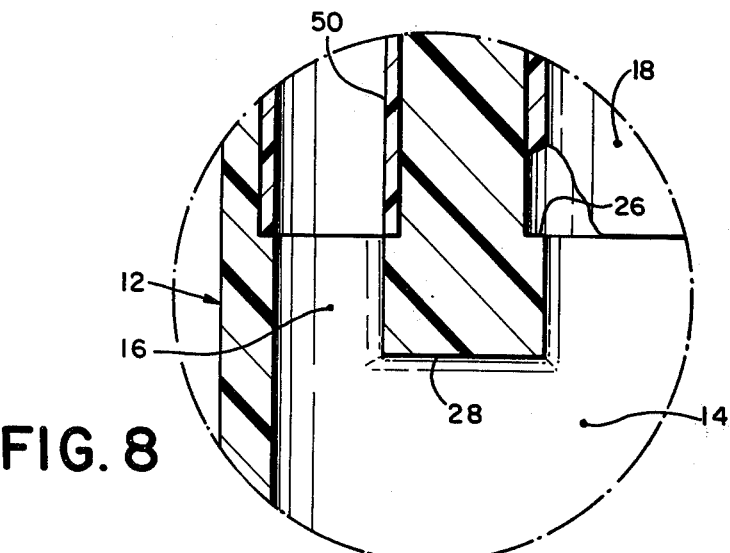
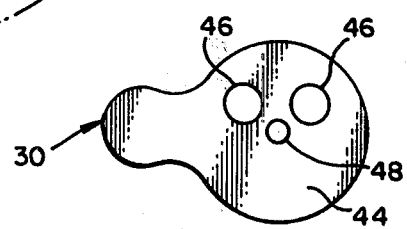
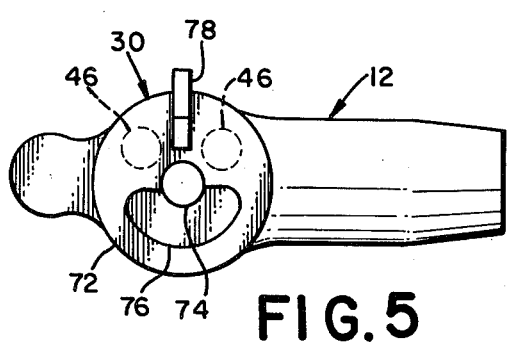

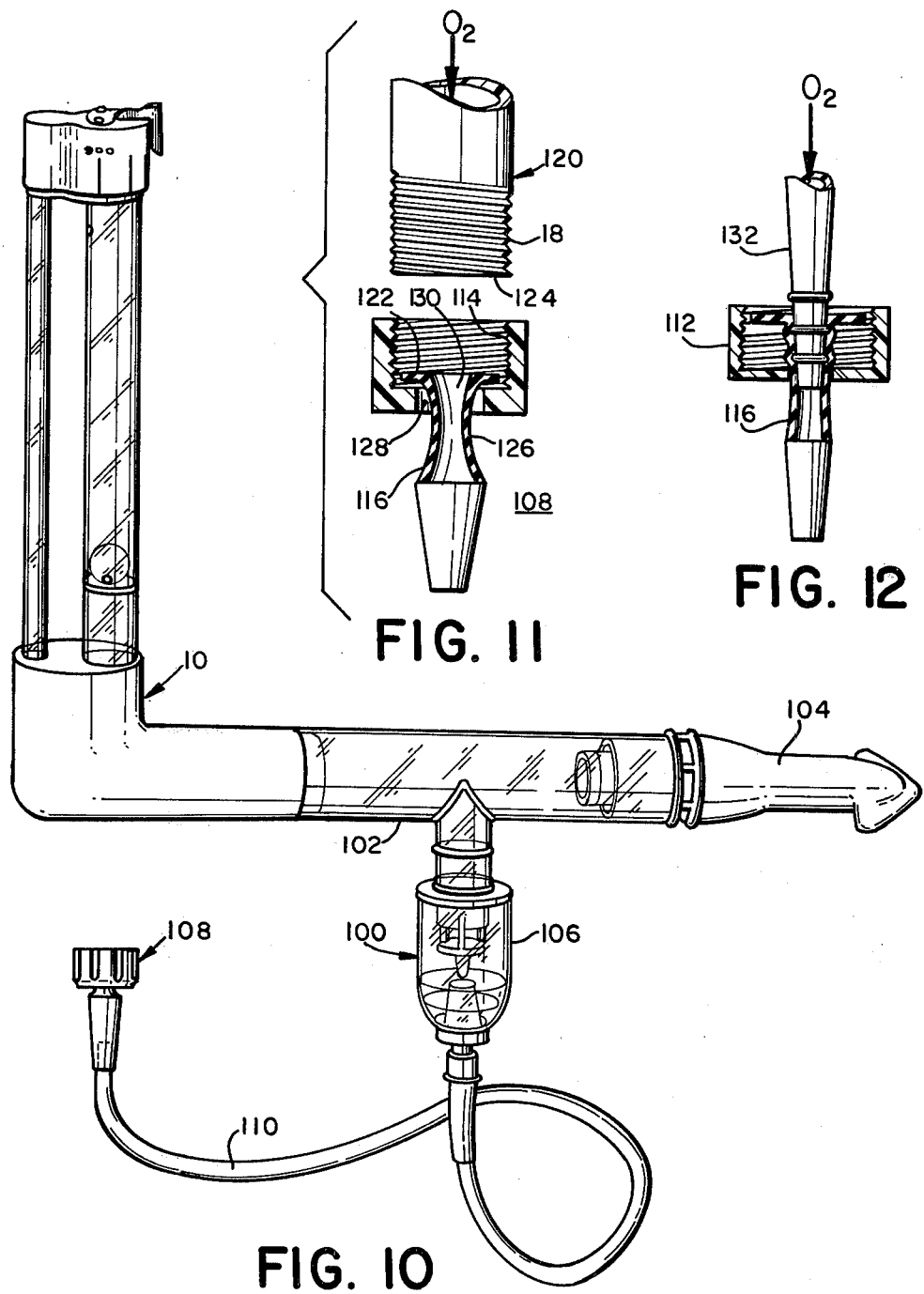

BREATHING EXERCISER

Cross-References

This application is a continuation-in-part of copending application Ser. No. 363,793, filed Mar. 31, 1982.

Background of the Invention

1. Field of the Invention

This invention relates generally to the field of respiratory therapeutic apparatus, and in particular, to a breathing exerciser for monitoring and controlling the tidal volume of inspired air, and indirectly, for controlling the rate of inspiration of medicine in vapor form.

2. Description of Prior Art

Inhalation and respiratory therapists have long recognized the need for patient-operated apparatus which accurately monitored the rate of air inhalation, often measured in cubic centimeters per second (cc/sec). The amount of air is often referred to as the tidal volume. The ability to inhale a sufficient tidal volume of air can be proscribed under several circumstances. One such circumstance is the postoperative loss of spontaneous deep breaths, which is among the respiratory complications which can result from abdominal and thoracic surgery. Another such circumstance is in the application of medicines which are in the form of vapors. Such medicines are inspired at dosage rates which are dependent upon rates of inhalation, that is, the tidal volume flowing in and out of the lungs. The greater the rate, or the greater the tidal volume, the greater the dosage rate of the medicine.

In accordance with these circumstances, there have been developed a number of so-called breathing exercisers which are addressed to the problems of patients under such circumstances.

Heretofore, all such apparatus have proven expensive to manufacture, awkward to use, difficult to clean (disinfect, pasteurize and/or sterilize), incapable of adjustment and incompatible with other respiratory therapeutic apparatus. This invention overcomes each of the difficulties noted above. With regard to ease and expense of manufacture, this invention comprises principally three molded members, two tubular stock members and a floatable or fluidizable ball, the ball being commercially available in a variety of sizes and weights. The device is relatively small, lightweight and is operated in an orientation which makes it very easy for a patient to monitor his tidal volume by watching the fluidizable ball. The major components of the apparatus are press-fitted together, and so may be easily disassembled, cleaned and reassembled, even by the patient. A simple adjustment means is provided which limits and delimits maximum fluid flow rates through the exerciser, providing calibrated adjustment. Finally, the exerciser may be easily attached, and used in conjunction with other respiratory therapeutic apparatus, such as nebulizers.

Summary of the Invention

It is an object of this invention to provide a breathing exerciser with which a patient can easily monitor and control his or her tidal volume of inspired air.

It is another object of this invention to provide such a breathing exerciser which is relatively simple and inexpensive to manufacture.

It is still another object of this invention to provide such a breathing apparatus which is simple to use, without the need for constant supervision.

It is yet another object of this invention to provide such a breathing exerciser which is easy to disassemble, clean and reassemble, without professional assistance.

It is yet another object of this invention to provide such a breathing exerciser which is adjustable, for controlling fluid flow rates therethrough, in order to facilitate different breathing therapy programs.

It is yet another object of this invention to provide such a breathing exerciser which can be used in combination with other inhalation therapy apparatus, in order to accurately control the dosage rate of medicines administered in vapor form.

These and other objects are accomplished by a breathing exerciser, comprising: first and second tubes; a lower cap member, having means for receiving one end of each of the tubes, the lower cap having a passageway communicating between the first tube and a lower inlet/outlet opening; an upper cap member, having means for receiving the other ends of the tubes and a passageway communicating between both the tubes and an upper inlet/outlet opening; means closing the lower end of the second tube, establishing a through flowpath, from the upper inlet/outlet opening, through the first tube and out of the lower inlet/outlet opening; a floatable indicating member disposed in the second tube, above the closing means, the indicating member being upwardly movable during fluid flow along the flowpath from the upper inlet/outlet opening to the lower inlet/outlet opening, the degree of movement depending upon the rate of fluid flow; means for adjusting the effective cross-section of at least one point on the fluid flowpath, for controlling the flow rate in an effective range; and, means for calibrating the effective range, whereby the tidal volume of air inspired through the exerciser can be monitored and controlled.

In the presently preferred embodiment, the lower and upper cap members are molded from plastic, and hold transparent tubes therebetween. The first tube, forming part of the flowpath, has a substantially smaller diameter than the second tube, in which the floatable indicating member is disposed. The floatable indicating member is a lightweight ball, which might appear to be similar to a ping-pong ball. However, the floatable member is in fact preferred to be a solid, very lightweight ball which is manufactured to exacting specifications of weight and size in order that medication and therapy programs can be more precisely controlled. In one embodiment, the means closing the lower end of the second tube is a disk member pressed into the lower end of the tube, and secured therein. In another embodiment, the closing means is a solid web in the lower cap member, at the bottom of a bore into which the tube is inserted.

The adjustment means may comprise the upper cap member having at least one aperture therein, and a disk member rotatably attached to the upper cap member, and having at least one slot therein. Relative rotation of the disk member and the upper cap member will move the aperture and slot into and out of correspondence with one another, effectively limiting and delimiting maximum fluid flow rates along the flowpath. As fluid flows into the upper inlet/outlet opening, downwardly through the first tube, and out of the lower inlet/outlet opening, a suction effect is created in the second tube, which causes the indicating member to rise in the tube.

For a given flow rate, the floatable member will move upwardly a corresponding distance. The exerciser is most easily calibrated by requiring the patient to breath with just the sufficient amount of effort to raise the floatable member to the top of the second tube. As the adjusting means are operated to increase the size of the inlet/outlet opening, a lower fliud flow rate will be required to move the indicating member. As the adjustment means are operated to decrease the effective size of the upper inlet/outlet opening, greater fluid flow rates will be required to create the suction effect necessary to raise the indicating member. The adjustment means can itself be calibrated within a desired range by providing one or more openings in the second tube in two locations. Openings immediately above the floor make the floatable member easier to raise. Openings adjacent the upper cap member make the floatable member harder to raise. In this fashion, the tidal volume of a patient can be easily monitored and controlled during therapeutic exercises.

The lower cap member is provided with a tapered end adjacent the inlet/outlet opening, so that it may be easily connected, by press-fitting, to other inhalation therapy apparatus, such as nebulizers for administering medicine in vapor form. The medicine is administered by a suction effect which is based upon the respiration rate and tidal volume of the patient. By using the exerciser according to this invention in conjunction with such inhalation therapy apparatus, the dosage rate of the medicine can be very precisely controlled.

Moreover, an exerciser according to this invention is held together by frictional, press-fitted joints. Accordingly, the exerciser can be easily disassembled into five major components, namely: the lower cap member, the upper cap member, the first tube, the second tube and the indicating member, which can then be easily cleaned (disinfected, pasteurized, and/or sterilized) and reassembled.

Brief Description of the Drawings

For the purpose of illustrating the invention, there are shown in the drawings forms which are presently preferred; it being understood, however, that this invention is not limited to the precise arrangements and instrumentalities shown.

FIG. 5 is a top plan view of FIG. 1;

FIG. 6 is a top plan view of FIG. 4;

FIG. 7 is a section view taken along the line VII—VII in FIG. 2;

FIG. 8 is an enlarged view of the circled portion of FIG. 2 designated VIII;

FIG. 9 is a partial section view, of an alternative embodiment of the invention; and, FIG. 10 is a diagrammatic representation of a breathing apparatus according to this invention in conjunction with inhalation therapeutic apparatus for administering medicine in vapor form;

FIG. 11 is a partial section view of the connector in FIG. 10 attached to an oxygen source with a threaded outlet coupling; and, FIG. 12 is a partial section view of the connector in FIG. 10 attached to an oxygen source with a nipple-type outlet coupling.

Detailed Description of the Preferred Embodiments

Figure 1:
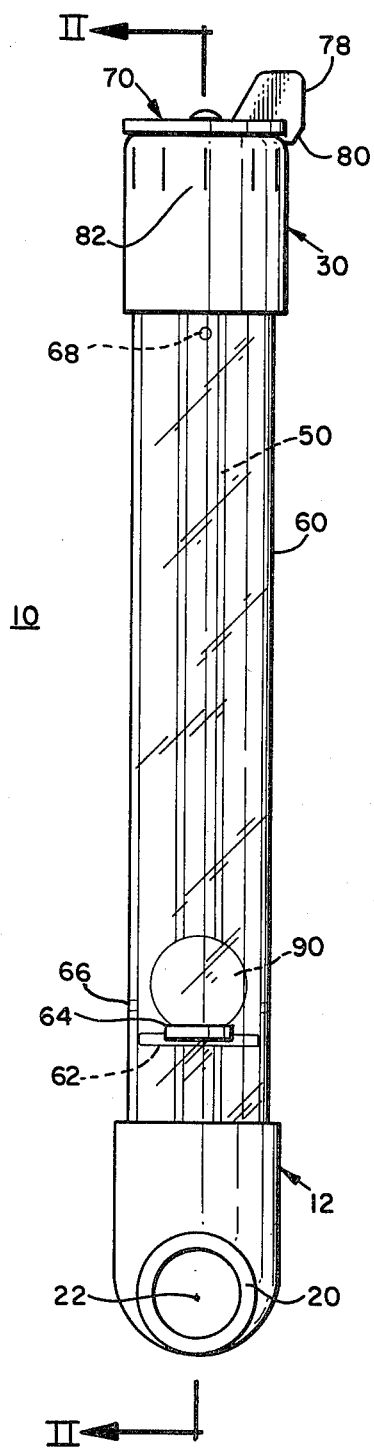
FIG. 1 is a front elevation of a breathing exerciser according to this invention.
Figure 2:
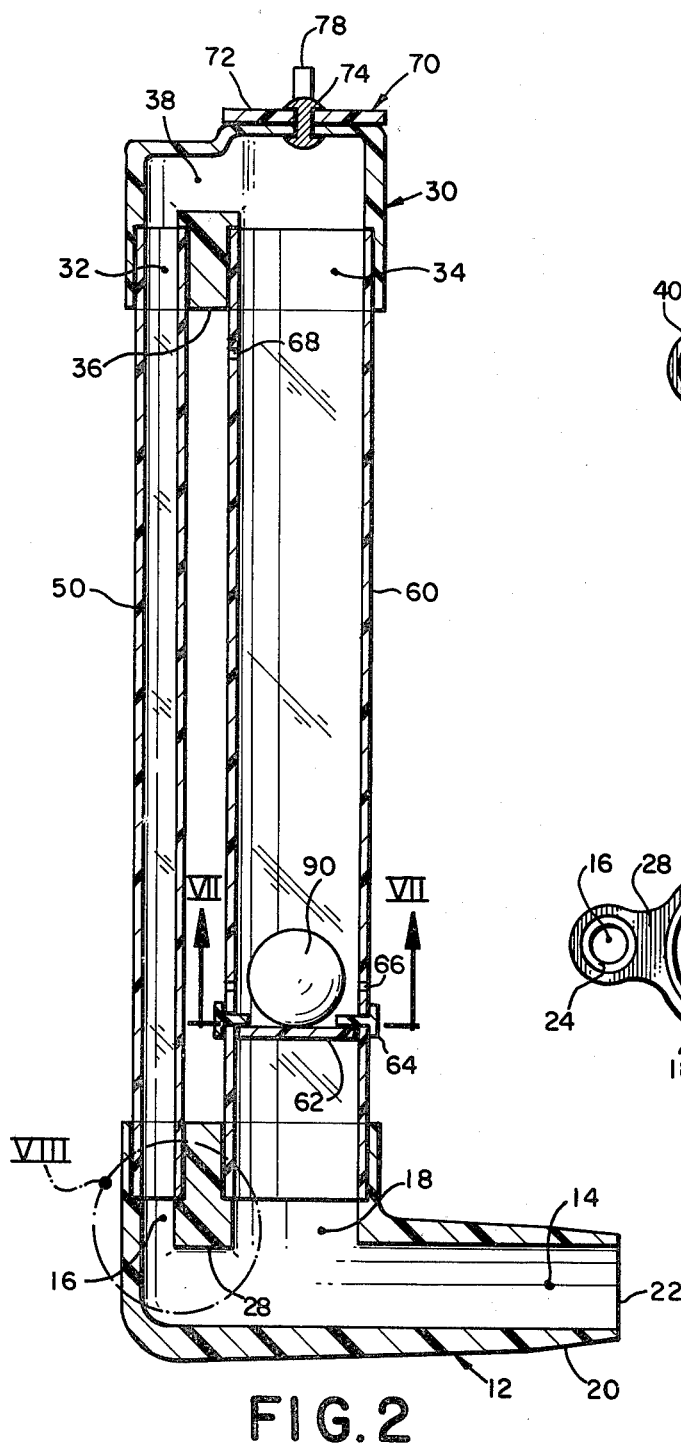
FIG. 2 is a section view taken along the line II—II in FIG. 1.

A breathing exerciser according to this invention is shown in FIGS. 1 and 2, and generally designated 10. The exerciser is used in an upright position which is illustrated in FIGS. 1 and 2. Accordingly, where reference is made throughout the description to "upper" and "lower," such reference is being made with respect to the orientation of FIGS. 1 and 2.

The exerciser comprises a lower cap member 12, an upper cap member 30, a first tube 50, a second tube 60, a valve assembly 70, means for calibrating the effective range of the valve assembly, and a floatable or fluidizable indicating member 90.

Figure 3:
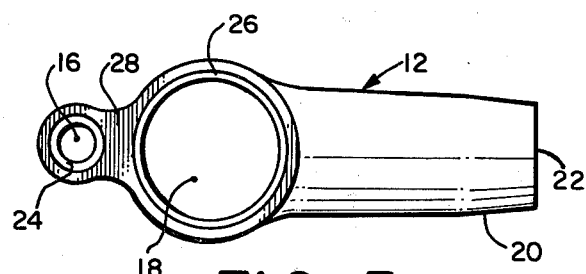
FIG. 3 is a top plan view of the lower cap member of FIG. 1; disassembled from the whole.

The lower cap member 12 is provided with a lateral bore 14, and first and second vertical bores 16 and 18, respectively. Lower cap member 12 has a tapered end 20 which terminates at an inlet/outlet opening 22. Vertical bores 16 and 18 are separated by a web 28. With further reference to FIGS. 3 and 8, the portion of lower cap member 12 defining the first bore 16 is provided with a shoulder 24 for receivingthe edge of the lower end of the first tube 50. The portion of lower cap member 12 defining the second vertical bore 18 is provided with a shoulder 26 for receiving the edge of the lower end of the second tube 60. It can be seen that when the lower end of tube 50 is press-fitted into the first vertical bore 16, with shoulder 24 forming an abutment, the first vertical bore 16 and lateral bore 14 form a passageway communicating between the interior of tube 50 and the inlet/outlet opening 22 of the lower cap member 12.

Figure 4:
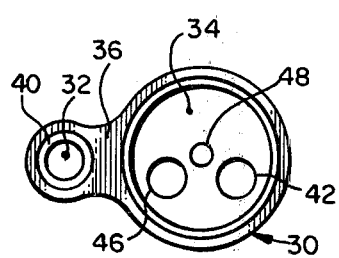
FIG. 4 is a bottom plan view of the upper cap member of FIG. 1, disassembled from the whole.

The upper cap member 30 is provided with its own first vertical bore 32 for receiving the upper end of the first tube 50, and its own second vertical bore 34 for receiving the upper end of the second tube 60. Vertical bores 32 and 34 are separated by a web 36 of the upper cap member. The vertical bores 32 and 34 are connected to one another by a lateral bore 38 forming a chamber in the upper cap member. With further reference to FIG. 4, the portion of the upper cap member defining the vertical bore 32 forms a shoulder 40 for receiving the edge of the upper end of the first tube 50. The portion of the upper cap member defining the vertical bore 34 forms a shoulder 42 for receiving the edge of the upper end of the second tube 60. An uppermost portion 44 is provided with two apertures 46 which together form an upper inlet/outlet opening. Finally, the uppermost portion is also provided with an aperture 48 for attaching the valve assembly 70.

The first tube 50 is an elongated hollow member of circular cross-section. It provides a communicating passageway between the vertical bore 16 of lower cap member 12 and the vertical bore 32 of upper cap member 30. First tube 50 is of substantially smaller diameter than second tube 60.

Second tube 60 is also an elongated hollow member of circular cross-section. Second tube 60 provides a guideway for the floatable indicating member 90. Although second tube 60 is connected to lower cap member 12, and its lower end is open to, and in communication with vertical bore 18, it is intended to be in fluid communication only with the chamber 38 of upper cap member 30. In order to seal the lower end of the second tube 60, a floor member in the form of a sealing disk 62 is placed in the tube 60. With further reference to FIG.

7, two insertion guides 64 may be inserted into the tube 60 through slots in the tube. The insertion guides 64 form an abutment surface for correctly fixing the position of the sealing disk 64. After being so inserted, sealing disk 62 can be glued or otherwise permanently attached. Sealing disk 62 also provides a stop which limits downward movement of the indicating member.

An alternative means for sealing the lower end of the second tube 60 is shown in FIG. 9. A lower cap member 12' is provided with a lateral bore 14' and a first vertical bore 16' as in the embodiment shown in FIG. 2. However, the second vertical bore 18' does not communicate with the lateral bore 14'. Instead, web portion 28' extends across the bottom thereof, effectively sealing the lower end of the second tube 60 from the passageway formed by vertical bore 16' and lateral bore 14'.

In accordance with the structure described thus far, a bidirectional fluid flowpath is established, although in practice, only one direction is of interest. In the direction of primary interest, which corresponds to a patient inhaling through the exerciser, fluid flows into the upper inlet/outlet opening formed by apertures 46, into chamber 38, down through vertical bore 32, through tube 50, down through vertical bore 16, along lateral bore 14 and out lower inlet/outlet opening 22. In the opposite direction, which corresponds to a patient exhaling into the breathing apparatus, the fluid flowpath enters the lower inlet/outlet opening 22, through lateral bore 14, up lateral bore 16, through first tube 50, into vertical bore 32, into chamber 38 and out through the upper inlet/outlet opening formed by apertures 46. Although the floatable indicating member 90 in the second tube 60 is not disposed directly in the fluid flowpath, it is nevertheless caused to be moved by fluid flow in the fluid flowpath. In particular, during inhalation, fluid "rushing" through chamber 38 and into tube 50 will create a suction or vacuum effect in tube 60. The suction or vacuum effect will or float the indicating member 90. As the indicating member becomes fluidized it will move upwardly in the tube 60. It can be appreciated that a certain flow rate of fluid moving in the fluid flowpath, corresponding to the tidal volume of air being inspired, will be just sufficient to raise the indicating member to the top of tube 60. If, however, the effective size of apertures 46 are decreased in some fashion, decreasing the amount of air which can flow therethrough, the suction or vacuum effect will also be decreased, making it harder to raise the indicating member. On the other hand, if the effective size of apertures 46 is increased in size, the suction or vacuum effect will be increased, and it will be easier to raise the indicating member. Accordingly, it can be seen that by adjusting the effective size of apertures 46 it is possible to control the amount of fluid flow necessary to raise the indicating member to the top of the tube.

The effective size of apertures 46 is controllably adjusted by valve assembly 70. Valve assembly 70 is mounted on the uppermost portion 44 of the upper cap member 30. The valve assembly 70 comprises a disk member 72 which is rotatably mounted to the cap member by a rivet or the like 74 which extends through aperture 48. Disk member 72 is provided with an arcuate slot 76. The radial width of the accurate slot 76 corresponds to the diameter of the apertures 46.

The disk member 72 may be provided with an upwardly projecting adjustment tab 78, having a portion 80 which extends somewhat downwardly below disk member 72. This lower extending portion 80 is positionable with a scale or guide rule 82 which can be printed or otherwise scribed on the outer surface of the upper cap member 30. This scale may also be provided on a decal.

With reference to FIG. 5, wherein apertures 46 are shown by dotted lines, as they are disposed under disk member 72, there is a position where there is no correspondence between the arcuate slot 76 and the apertures 46. In this position, the valve assembly has completely closed the fluid flowpath. If disk member 72 is rotated somewhat in either direction, for example, if the tab 78 is moved to an angle of 45° from vertical, one end of the arcuate slot 76 will partially overlie one or the other of apertures 46. If this rotation continues, there will eventually be a full correspondence between one of the apertures 46 and the arcuate slot 76. In this position, the valve assembly corresponds to opening the flowpath to the extent of 50%. If disk member 72 is further rotated, to a position 180° from that shown in FIG. 5 (tab 78 pointed downwardly in FIG. 5, or to the left in FIG. 1), there will be a full correspondence between both apertures 46 and the arcuate slot 76. In this position, the fluid flowpath will be open 100%. The valve assembly 70 provides a means by which the rate of fluid flow required to raise the indicating member can be easily and rather precisely controlled and regulated through limiting and delimiting the effective size of the upper inlet/outlet opening.

The range in which the valve assembly is effective can be calibrated or adjusted by providing at least one opening in at least two places on second tube 60. One position is immediately above sealing disk 62, that is, above the disk and below the horizontal center line of the ball 90 when it rests on the sealing disk. Openings 66 make it easier to raise ball 90. The other position is adjacent the upper cap member 30. Opening 68 makes it harder to raise ball 90. In the presently preferred embodiment there are three openings 66 and one opening 68. This arrangement provides adjustment over the most useful and typical tidal volumes, without requiring undue effort to raise the ball. In the embodiment of FIG. 9, at least one passageway 92 through lower cap member 12' is provided in place of openings 66.

Finally, although the floatable indicating member has the appearance of a simple ping-pong ball, ping-pong balls are in fact unsuitable, and it is preferred that the indicating member conform to accepted medical standards with respect to size, weight and material. In the presently preferred embodiment the ball 90 is solid, made from very lightweight material, and has a diameter only slightly less than the inner diameter of the second tube.

As can be appreciated particularly from FIG. 2, the breathing exerciser can be easily disassembled into its various components, as they are only press-fitted to one another. When so disassembled, it is relatively easy to clean the various components. Such cleaning may include disinfection, pasteurization and/or sterilization. In the event one of the components is broken, it is easy to replace that component. After cleaning, it is a relatively simple matter to reassemble the breathing exerciser. The only conceivable mistake that might be made in reassembling the exerciser would be inserting the second tube 60 upside down, although such a mistake would be immediately apparent as the indicating member 90 would fall into the lower cap member and be stuck there. Even this problem would be avoided in the embodiment illustrated in FIG. 9.

The various components of the breathing exerciser may be formed from plastic, enabling the upper and lower cap members to be molded. The tube members are standard stock, and require no special machining, except for the slots necessary to enable positioning of the insertion guides 64 and the calibration openings.

It should be apparent that the breathing exerciser disclosed and described herein provides a means by which a patient receiving respiratory therapy can engage in breathing exercises which can be easily monitored and controlled. The ability to monitor and control the tidal volume of respiratory patients can be utilized in the application of medicines in the form of a vapor, the form most frequently utilized for respiratory patients.

A breathing apparatus in accordance with this invention can be used in conjunction with an inhalation therapy apparatus, commonly referred to as a nebulizer, as shown diagrammatically in FIG. 10. The nebulizer 100 comprises a reservoir for a medicinal fluid, and means for a patient to inhale oxygen which has been saturated with vapor from the medicinal fluid. A T-connector 102 has one end attached to the tapered end 20 of exerciser 10 and the other end attached to mouthpiece 104. Tapered end 20 facilitates attachment to almost any other apparatus, for example, directly to mouthpiece 104 if the nebulizer is not utilized. Saturation usually occurs by a vacuum driven venturi jet in the atomization chamber 106. The jet is provided by metered oxygen supply, delivered to the atomizer through connector 108 and tube 110. The rate at which the medicine is administered depends upon the patient's tidal volume of inspired air. If the patient breathes faster and/or takes deeper breaths, more medicine will be delivered per breath. Accordingly, the dosage rate is ordinarily difficult to control. However, when the nebulizer is attached to a breathing exerciser according to this invention, wherein the patient will inhale in a manner which activates the fluidizable indicating member, adjustment of the breathing apparatus will enable the dosage rate of the medicine to be easily monitored and regulated. During therapy most of the interior of the exerciser serves as a reservoir to trap medicated vapors, and prevent them from being vented to the atmosphere. In this manner, medicine is used more efficiently as less is wasted. Although a patient can exhale through the nebulizer, it is usually only to monitor and control inhalation. Accordingly, nebulizers are often provided with valves for venting exhaled air. Such valves may also be used when the exerciser is included as part of the inhalation apparatus. In the absence of such valves, such patients can simply take the mouthpiece out of their mouths during exhalation.

Oxygen supplies, both fixed and portable, are provided with threaded outlet couplings or push-on nipple couplings. It is often strictly a matter of chance which kind of coupling will be found on the oxygen supply used by a patient at any given time or place. However, inhalation therapy apparatus to date have been provided with only one kind of coupling, placing the patient at some risk and inconvenience in locating a suitable oxygen source. Connector 108, however, is specially adapted for either kind of connection. With reference to FIGS. 11 and 12, connector 108 has a cap 112 with an interior threaded portion 114 and a section of rubber tube 116. Threaded portion 114 engages the outer threaded portion 118 of a threaded outlet coupling 120. The flat annular surface 122 of the end of tube 116 seals against the lower annular edge 124 of threaded outlet coupling 120. Tube 116 has a narrow section 126 which passes through a larger than otherwise necessary opening 128 in cap 112. Cap 112 can slide down the narrower section a sufficient distance to enable the end 130 of the tube 116 to be pressed directly onto the end of the nipple coupling 132. Cap 112 can then be pressed back upwardly, the inwardly facing surface of opening 128 pressing the tube against the nipple and holding it in place. The cap 112 is preferably molded from plastic.

In view of the ability of an exerciser according to this invention to provide adjustment of the fluid flow rates, a single size can be used by most persons. In the presently preferred embodiment, the overall height of the presently preferred embodiment is approximately 7 inches. The diameter of the smaller, first tube is approximately ¼ inch and the diameter of the larger, second tube is approximately ¾ of an inch. The lateral length of the lower cap member 12 is approximately 1½ inches and the diameter of the first inlet/outlet opening 22 is approximately ½ inch. The foregoing dimensions are illustrative only, and should not be deemed limiting in any sense. The dimensions are, however, a good illustration of the compactness of the invention.

This invention may be embodied in other specific forms without departing from the spirit or essential attributes thereof, and accordingly, reference should be made to the appended claims, rather than to the foregoing specification, as indicating the scope of the invention.

We claim:

1. A breathing exerciser, comprising:
    first and second tubes;
    a lower cap member, said lower cap member having means for receiving one end of each of the tubes, the lower cap member having a lower inlet/outlet opening defining a mouth-piece and a passageway communicating between the first tube and said lower inlet/outlet opening;
    an upper cap member, said upper cap member having means for receiving the other ends of the tubes and having an upper inlet/outlet opening and a passageway communicating between both the tubes and said upper inlet/outlet opening;
    means for closing the lower end of the second tube;
    a floatable indicating member disposed in the second tube, the indicating member being upwardly movable by a vacuum induced during fluid flow along a fluid flow path from the upper inlet/outlet opening, through the first tube and out of the lower inlet/outlet opening, the amount of movement depending upon the rate of fluid flow;
    means disposed in said upper inlet/outlet opening for adjustably limiting and delimiting the fluid flow rate in an effective range; and,
    means for calibrating the effective range of the adjusting means, including the second tube having at least one opening immediately above the closing means and at least one opening immediately below the upper cap member,
    whereby the tidal volume of air inhaled through the exerciser can be monitored and controlled.

2. The breathing exerciser of claim 1, wherein the upper cap member has at least one aperture therethrough comprising said upper inlet/outlet opening, and said means for limiting and delimiting the fluid flow rate comprising a valve disk, having at least one slot therethrough, the valve disk being rotatably attached to the upper cap member, whereby the slot of the valve disk can be adjustably moved into and out of a position corresponding to the at least one aperture.

3. The breathing exerciser of claim 1, wherein the means for closing the lower end of the second tube comprises a disk member sealably inserted into the tube member.

4. The breathing exerciser of claim 1, wherein the means for closing the lower end of the second tube comprises a web portion of the lower cap member, the lower cap member having at least one passageway communicating between the lower end of the second tube and exteriorly of the lower cap member.

5. The breathing exerciser of claim 1, wherein the lower cap member comprises a tapered end portion surrounding the lower inlet/outlet opening, whereby the exerciser can be easily connected, by frictional engagement, to tubes of different diameter.

6. The breathing exerciser of claim 1, wherein the tube receiving means in both the lower and upper cap members comprises structure defining receiving bores and abutment shoulders, the bores being so dimensioned as to enable the tubes to be pressed-fitted therein, whereby the exerciser may be easily disassembled and reassembled.

7. The breathing exerciser of claim 1, in combination with a nebulizer, said nebulizer having an output which is in fluid communication with the lower inlet/outlet opening, whereby the dosage of medicine dispensed by the nebulizer may be easily and reliably regulated.

* * * * *